Figure 1:
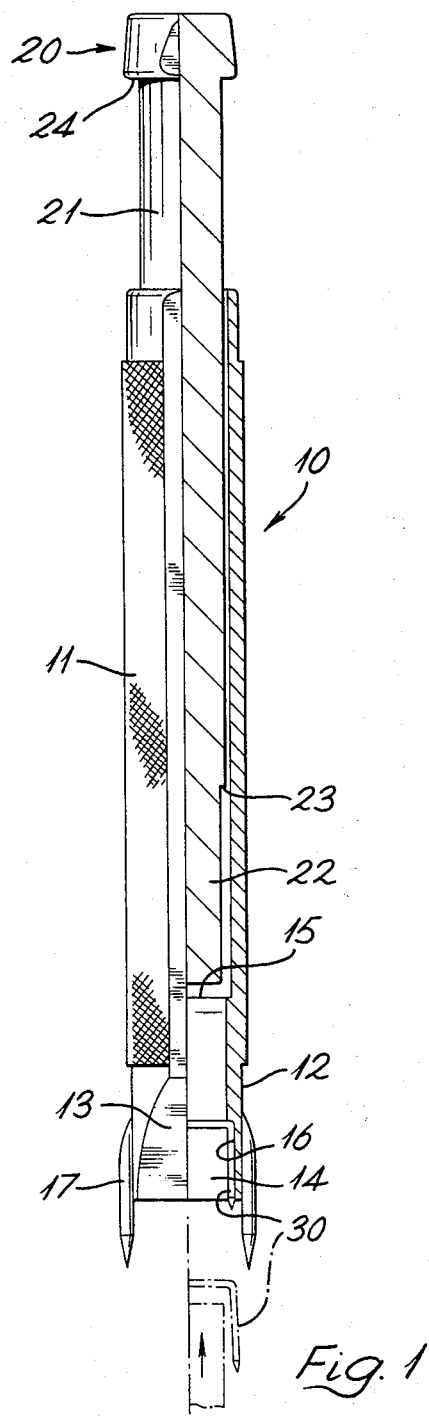

United States Patent [19]

McHarrie et al.

[11] 4,415,111
[45] Nov. 15, 1983

[54] STAPLING DEVICES

[76] Inventors: John C. McHarrie, 28 Hall Rd., Fulwood, Preston, Lancashire; Peter W. Hopcroft, 17 Balmoral Dr., Formby, Liverpool, Lancashire; Donald B. Case, 'Alderley', 6 Church Ave., Penwortham, Preston, Lancashire, all of England

[21] Appl. No.: 256,613

[22] Filed: Apr. 22, 1981

[30] Foreign Application Priority Data

Apr. 22, 1980 [GB] United Kingdom ................ 8013230

[51] Int. Cl.³ .......................... A61B 17/18; B25C 5/02
[52] U.S. Cl. ................................ 227/19; 227/DIG. 1; 227/147
[58] Field of Search .................. 227/19, DIG. 1, 147; 128/334 R, 335

[56] References Cited

U.S. PATENT DOCUMENTS

| 1,340,705 | 5/1920 | Lander | 227/147 |
| 2,330,575 | 9/1943 | Grauding | 227/147 |
| 4,122,989 | 10/1979 | Kapitanov et al. | 227/19 X |
| 4,263,903 | 4/1981 | Griggs | 227/DIG. 1 |
| 4,299,021 | 11/1981 | Williams | 227/147 X |

Primary Examiner—Paul A. Bell
Attorney, Agent, or Firm—Cushman, Darby & Cushman

[57] ABSTRACT

A stapling device developed for orthopaedic use is in two cooperable parts including: a locator (10) in the form of a generally tubular member having a pair of opposed parallel grooves (16) extending longitudinally over one end portion of the inner surface of the member to receive the legs of a staple (30) of appropriate size entered head first into the one end, and having pin or other penetrating means (17) projecting from the one end of the member for a short length compared to the grooves to be entered into bone or other material to stabilize the locator in a desired position relative thereto; and a punch (20) longer than the locator and slidable therein over substantially the whole locator length from its other end to drive a staple therefrom. The one end portion of the locator preferably has its interior narrowed to a slot form (14) with the grooves at the slot ends, and its exterior tapered or otherwise similarly shaped with pins at each end adjacent the grooves, to facilitate staple location. Also the locator and punch preferably incorporate stop formations (15, 23; 24) to obviate undue penetration of a driven staple.

4 Claims, 2 Drawing Figures

U.S. Patent    Nov. 15, 1983    4,415,111

STAPLING DEVICES

This invention concerns stapling devices and more particularly, but not exclusively, such devices for the insertion of orthopaedic staples into bone during surgery.

The insertion of orthopaedic staples commonly involves the separate use of two or more instruments, including one to locate the staple with an initial, relatively short penetration, and a punch for completion of the penetration. No initial guidance or rigid location of the staple is effected and, in consequence, a first blow by way of the punch which is other than very closely aligned with the staple will normally cause the staple to tilt from the desired orientation relative to the bone. Also, there is a tendency for the staple to splay out during initial securement, orthopaedic staples being made, in common with other staples, with slightly divergent legs.

It should be noted that other existing stapling instruments, in particular staple guns, which would appear to resolve the difficulties just discussed, are not suitable for use with orthopaedic staples. Orthopaedic staples are normally inserted within confined sites which will frequently not permit ready access for a staple gun. Also, staple guns are designed for multiple insertion of staples from a magazine, whereas orthopaedic staples are made individually and are usually inserted in small numbers in any one situation. In addition, staple guns are complex instruments to the extent that repeated sterilisation for surgical use would be problematical.

In any event an object of the present invention is to reduce the difficulties of orthopaedic staple insertion and, to this end, provides a stapling device comprising: a staple locator in the form of a generally tubular member having a pair of parallel grooves extending in opposed relation longitudinally partway along the inner surface thereof from one end, and having pin or like bone penetrating means connected to said member and projecting longitudinally therefrom at said one end for a short length relative to that of said grooves; and a punch member longer than said tubular member and slidably locatable therein over substantially the whole length of the latter member from the other end thereof.

In use of the proposed instrument a staple of appropriate size is located head first into the one end of the locator with the staple legs being individually received in the grooves of the locator. The locator is then positioned with its one end to locate the staple over and in planar alignment with its desired disposition when inserted, and the locator driven at its other end to stabilise this position by way of its penetration means. Thereafter, the punch is used, by insertion in the other end of the locator, to drive the staple into the adjacent bone.

Regarding the size of the staple: its width should correspond to that between the locator grooves, and its depth can be such as to allow total reception in the grooves, or slight projection therefrom but to a lesser extent than that of the penetration means.

Preferably, the punch member is also slidably receivable in the one end of the tubular member, at least substantially wholly over the length of the grooves therein. In this event the punch can be used to push a staple fully into the locator. Such loading of a staple is advantageous insofar as the staple will normally be slightly splayed and will be gripped within the locator if firmly pushed into the parallel grooves of the latter.

Figure 2:
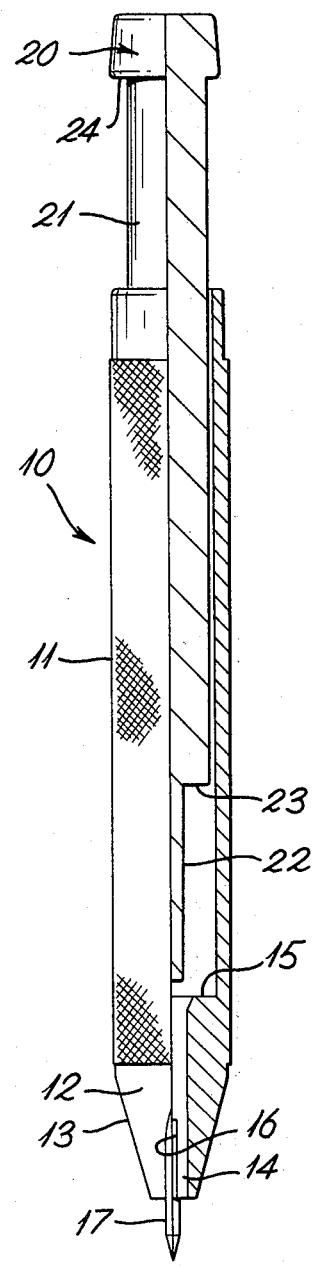

In order that the invention as so far discussed above may be clearly understood, the same will now be more fully described, by way of example, with reference to the accompanying drawings, in which:

FIGS. 1 and 2 respectively illustrate one embodiment of the invention in mutually perpendicular partial sectional views.

The illustrated device comprises a locator 10 and a punch 20, a staple also being indicated at 30.

The locator 10 comprises a generally tubular member having an upper portion 11 of substantially hollow circular cylindrical form leading to a lower portion 12 which is tapered by the provision of diametrically opposed external flats 13 and has a correspondingly narrowed, slot form interior 14. The interior 14 communicates with that of the upper portion to define a shoulder 15 within the locator. In addition, the interior 14 has two opposed parallel grooves 16 formed therein and extending longitudinally therealong from the lower free end of the locator. These grooves 16 are located at the narrow ends of the slot-shaping of interior 14.

A remaining feature of the locator 10 is the provision of two pins 17 respectively located adjacent the grooves 16, but spaced therefrom at the outer surface of the locator, to project from the lower free end in parallel manner a short length relative to that of the grooves and in planar alignment therewith.

The punch 20 comprises a member having upper and lower portions 21 and 22 meeting at a shoulder 23 and complementary with the corresponding interior of the locator portions 11 and 12, but with portion 21 longer than 11, and portion 22 slightly shorter than 12. The punch upper portion 22 is also radially expanded by a collar formation 24 located at a distance therealong from the shoulder 23 equal to that of the locator upper portion 11 between its shoulder 15 and free end.

Use of the illustrated device is laregly self-evident from the early description above of the invention. The staple 30 is introduced head first into the free end of locator portion 12, with the staple legs located in the grooves 16, and the staple can then be driven fully into the locator to abut the ends of the grooves by use of the punch.

The staple 30 is shown in this fully loaded position to project slightly from the locator, but to a lesser extent than the pins 17. This represents a maximum staple length, but shorter lengths can be used providing the width corresponds to that between the locator grooves.

The staple is also shown in broken outline before introduction in the locator in association with a similar partial illustration of the punch. The staple will be seen to be slightly splayed, and will accordingly be compressed upon loading and therefore gripped in the locator.

Once loaded, the locator is positioned above the desired staple location, and lightly directly driven to penetrate the pins into the relevant bone and so stabilise the locator. The punch is then entered into the upper end of the locator as shown and hammered to drive the staple into the bone. This driving is terminated when the punch collar 24 abuts the upper end of the locator, and the punch shoulder 23 at the same time just reaches the shoulder 15 within the locator, the collar and shoulder locations being such that the staple is not driven excessively but to locate its head on the bone surface.

The benefits of this device are that the locator affords stabilised location and guidance for the staple when driven. Also positioning of the pins externally of the locator and in planar alignment with the staple-receiving grooves facilitates positioning of the locator relative to the desired staple securement site in the bone. This last positioning is further facilitated, as is the more general access of the device to an operation site, by the tapered form of the lower portion of the locator.

While the invention has been described with more particular reference to the illustrated embodiment, this is not intended to limit the invention which is capable of variation within the terms of the broader initial discussion thereof. For example, while it is presently preferred to employ a device which, as shown, is adapted for a single width of staple, a multi-width embodiment is clearly possible by the provision of suitable additional grooving in the locator. Also, the illustrated embodiment is a development from another which had no collar 24, but occasionally was subject to jamming between its punch and locator at the shoulders 23 and 15. The collar has obviated this difficulty and so another embodiment need have no shoulders.

We claim:

1. An orthopaedic stapling device comprising:
    a staple locator in the form of a tubular member having an inner surface narrowed towards a slot shape at one end thereof and an external surface tapered towards said one end to conform generally with said slot shape, said member having a pair of like parallel grooves extending in opposed relation longitudinally part-way along said inner surface from said one end, said member having a pair of bone penetrating pins connected thereto and projecting longitudinally therefrom at said one end for a short length relative to that of said grooves, said pairs of grooves and pins each being located respectively adjacent to the ends of said slot shape;
    a bone penetrating staple having a bridge portion and a pair of leg portions projecting in slightly divergently splayed manner from the opposite ends of the former, said bridge portion having a length equal to the spacing between said locator member grooves, said leg portions having mutually like length not substantially greater than the length of said grooves, and said staple being substantially wholly-locatable within said locator member, bridge portion first, with said leg portions engaged under compression respectively in said grooves; and
    a punch member longer than said tubular member and slidably locatable therein over substantially the whole length of the latter member from the other end thereof, and also slidably locatable in said locator member one end subtantially wholly over the length of said grooves.

2. A device according to claim 1 comprising stop means on said punch member to limit passage thereof through said locator member from said other end thereof to a position within said locator member and closely adjacent to said one end thereof.

3. A device according to claim 2 wherein said stop means comprises a collar to abut said other end of said locator member.

4. A device according to claim 2 wherein said stop means comprises a shoulder formation, to abut a complementary shoulder formation within said locator member.

* * * * *